US008932282B2

(12) United States Patent
Gilbert (10) Patent No.: US 8,932,282 B2
(45) Date of Patent: Jan. 13, 2015

(54) POWER LEVEL TRANSITIONING IN A SURGICAL INSTRUMENT

(75) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1184 days.

(21) Appl. No.: 12/534,308

(22) Filed: Aug. 3, 2009

(65) Prior Publication Data

US 2011/0028963 A1   Feb. 3, 2011

(51) Int. Cl.
*A61B 18/10* (2006.01)
*A61B 18/12* (2006.01)
*A61B 18/14* (2006.01)
*A61B 18/00* (2006.01)

(52) U.S. Cl.
CPC ..... *A61B 18/1206* (2013.01); *A61B 2018/1412* (2013.01); *A61B 18/1445* (2013.01); *A61B 2018/00702* (2013.01); *A61B 2018/1455* (2013.01); *A61B 2018/0063* (2013.01); *A61B 2018/00875* (2013.01)
USPC .............................................. 606/34; 606/41

(58) Field of Classification Search
USPC .......................................... 606/32–35, 37–42
See application file for complete search history.

(56) References Cited

U.S. PATENT DOCUMENTS

| 4,100,505 | A | * | 7/1978 | Belt et al. ................. 331/71 |
|---|---|---|---|---|
| 4,188,927 | A | | 2/1980 | Harris |
| 4,590,934 | A | | 5/1986 | Malis et al. |
| 4,727,874 | A | | 3/1988 | Bowers et al. |
| 4,739,759 | A | | 4/1988 | Rexroth et al. |
| 4,788,634 | A | | 11/1988 | Schlecht et al. |
| 4,903,696 | A | | 2/1990 | Stasz et al. |
| 5,075,839 | A | | 12/1991 | Fisher et al. |

(Continued)

FOREIGN PATENT DOCUMENTS

| DE | 179607 | 3/1905 |
|---|---|---|
| DE | 1099658 | 2/1961 |

(Continued)

OTHER PUBLICATIONS

Wald et al., "Accidental Burns", JAMA, Aug. 16, 1971, vol. 217, No. 7, pp. 916-921.

(Continued)

*Primary Examiner* — Michael Peffley (57) ABSTRACT

An electrosurgical system and method are disclosed. The system includes an electrosurgical generator adapted to supply electrosurgical energy to tissue. The generator is further adapted to supply an electrosurgical signal at a variable power level. The generator includes sensor circuitry adapted to sense tissue impedance and/or an electrosurgical signal zero crossing. The generator also includes a controller, which may include a microprocessor, that is adapted to receive a tissue impedance signal and/or a waveform zero crossing signal. The controller is configured to monitor tissue impedance, and in response to a threshold value of impedance being reached, to cause a power level of the electrosurgical energy to transition from a first power level to a second power level. The slew rate of the power transition may be in accordance with a transition function, such as a cosine function. The power transition may additionally or alternatively be performed during, or correlated with, an electrosurgical signal zero crossing. The system also includes an electrosurgical instrument including at least one active electrode adapted to apply electrosurgical energy to tissue for treatment.

15 Claims, 7 Drawing Sheets

(56) References Cited

U.S. PATENT DOCUMENTS

| | | | |
|---|---|---|---|
| 5,119,284 | A | 6/1992 | Fisher et al. |
| 5,152,762 | A | 10/1992 | McElhenney |
| 5,249,121 | A | 9/1993 | Baum et al. |
| RE34,432 | E | 11/1993 | Bertrand |
| 5,318,563 | A | 6/1994 | Malis et al. |
| 5,348,554 | A | 9/1994 | Imran et al. |
| 5,370,645 | A | 12/1994 | Klicek et al. |
| 5,383,874 | A | 1/1995 | Jackson et al. |
| 5,423,809 | A | 6/1995 | Klicek |
| 5,423,811 | A | 6/1995 | Imran et al. |
| 5,496,312 | A * | 3/1996 | Klicek ............ 606/34 |
| 5,540,681 | A | 7/1996 | Strul et al. |
| 5,545,161 | A | 8/1996 | Imran |
| 5,599,344 | A | 2/1997 | Paterson |
| 5,651,780 | A | 7/1997 | Jackson et al. |
| 5,688,267 | A | 11/1997 | Panescu et al. |
| 5,697,927 | A | 12/1997 | Imran et al. |
| 5,722,975 | A | 3/1998 | Edwards et al. |
| 5,735,846 | A | 4/1998 | Panescu et al. |
| 5,827,271 | A | 10/1998 | Buysse |
| 6,053,912 | A | 4/2000 | Panescu et al. |
| 6,055,458 | A | 4/2000 | Cochran et al. |
| 6,056,745 | A | 5/2000 | Panescu et al. |
| 6,056,746 | A | 5/2000 | Goble et al. |
| 6,093,186 | A | 7/2000 | Goble |
| 6,142,992 | A | 11/2000 | Cheng et al. |
| 6,231,569 | B1 * | 5/2001 | Bek et al. ............ 606/34 |
| 6,235,020 | B1 | 5/2001 | Cheng et al. |
| 6,261,286 | B1 | 7/2001 | Goble et al. |
| 6,293,941 | B1 | 9/2001 | Strul et al. |
| 6,293,942 | B1 | 9/2001 | Goble et al. |
| 6,306,134 | B1 | 10/2001 | Goble et al. |
| 6,364,877 | B1 | 4/2002 | Goble et al. |
| 6,416,509 | B1 | 7/2002 | Goble et al. |
| 6,428,537 | B1 | 8/2002 | Swanson et al. |
| 6,488,678 | B2 | 12/2002 | Sherman |
| 6,565,562 | B1 | 5/2003 | Shah et al. |
| 6,656,177 | B2 | 12/2003 | Truckai et al. |
| 6,730,078 | B2 | 5/2004 | Simpson et al. |
| 6,740,079 | B1 | 5/2004 | Eggers et al. |
| 6,843,789 | B2 | 1/2005 | Goble |
| 6,855,141 | B2 | 2/2005 | Lovewell |
| 6,875,210 | B2 | 4/2005 | Refior et al. |
| 6,893,435 | B2 | 5/2005 | Goble |
| 6,923,804 | B2 | 8/2005 | Eggers et al. |
| 6,939,347 | B2 | 9/2005 | Thompson |
| 6,948,503 | B2 | 9/2005 | Refior et al. |
| 6,962,587 | B2 | 11/2005 | Johnson et al. |
| 6,989,010 | B2 | 1/2006 | Francischelli et al. |
| 7,001,379 | B2 | 2/2006 | Behl et al. |
| 7,062,331 | B2 | 6/2006 | Zarinetchi et al. |
| 7,066,933 | B2 * | 6/2006 | Hagg ............ 606/34 |
| 7,195,627 | B2 | 3/2007 | Amoah et al. |
| 7,211,081 | B2 | 5/2007 | Goble |
| 7,223,264 | B2 | 5/2007 | Daniel et al. |
| 7,226,447 | B2 | 6/2007 | Uchida et al. |
| 7,250,048 | B2 | 7/2007 | Francischelli et al. |
| 7,341,586 | B2 | 3/2008 | Daniel et al. |
| 7,655,003 | B2 * | 2/2010 | Lorang et al. ............ 606/32 |
| 8,152,802 | B2 | 4/2012 | Podhajsky et al. |
| 8,162,932 | B2 | 4/2012 | Podhajsky et al. |
| 8,167,875 | B2 | 5/2012 | Podhajsky et al. |
| 8,174,267 | B2 | 5/2012 | Brannan et al. |
| 8,180,433 | B2 | 5/2012 | Brannan et al. |
| 8,211,100 | B2 | 7/2012 | Podhajsky et al. |
| 8,226,639 | B2 | 7/2012 | Podhajsky et al. |
| 8,242,782 | B2 | 8/2012 | Brannan et al. |
| 8,248,075 | B2 | 8/2012 | Brannan et al. |
| 8,257,349 | B2 | 9/2012 | Orszulak |
| 8,287,527 | B2 | 10/2012 | Brannan et al. |
| 8,287,528 | B2 | 10/2012 | Wham et al. |
| 8,287,529 | B2 | 10/2012 | Orszulak |
| 8,333,759 | B2 | 12/2012 | Podhajsky |
| 8,346,370 | B2 | 1/2013 | Haley et al. |
| 8,377,053 | B2 | 2/2013 | Orszulak |
| 8,403,924 | B2 | 3/2013 | Behnke et al. |
| 8,409,186 | B2 | 4/2013 | Behnke et al. |
| 8,734,444 | B2 | 5/2014 | Kerr |
| 2003/0181898 | A1 | 9/2003 | Bowers et al. |
| 2003/0229344 | A1 | 12/2003 | Dycus |
| 2005/0203504 | A1 * | 9/2005 | Wham et al. ............ 606/34 |
| 2008/0071257 | A1 | 3/2008 | Kotmel |
| 2009/0254077 | A1 | 10/2009 | Craig |
| 2010/0082083 | A1 | 4/2010 | Brannan et al. |
| 2010/0094271 | A1 | 4/2010 | Ward et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 880220 | 6/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | 98/27880 | 7/1998 |
| WO | 02/47565 | 6/2002 |

OTHER PUBLICATIONS

Chicharo et al. "A Sliding Goertzel Algorith" Aug. 1996, pp. 283-297 Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone" Neurosurgery 15:(1984) pp. 945-950.

(56) References Cited

OTHER PUBLICATIONS

Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report EP10171787 dated Nov. 18, 2010.
U.S. Appl. No. 10/406,690, filed Apr. 3, 2003, Michael S. Klicek.
U.S. Appl. No. 10/543,713, filed Mar. 2006, Robert H. Wham.
U.S. Appl. No. 11/242,458, filed Oct. 3, 2005, Daniel J. Becker.

* cited by examiner

POWER LEVEL TRANSITIONING IN A SURGICAL INSTRUMENT

BACKGROUND

1. Technical Field

The present disclosure relates to electrosurgical apparatuses, systems and methods. More particularly, the present disclosure is directed to an electrosurgical control system that provides improved power curve transition response.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of radiofrequency (RF) electrical current to a surgical site to cut, ablate, coagulate or seal tissue.

In bipolar electrosurgery, one of the electrodes of the handheld instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

Bipolar electrosurgical techniques and instruments can be used to coagulate blood vessels or tissue, e.g., soft tissue structures, such as lung, brain and intestine. For example, a surgeon can cauterize, coagulate, desiccate, or simply reduce bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, and so forth.

In monopolar electrosurgery, the active electrode is typically a part of the surgical instrument held by the surgeon that is applied to the tissue to be treated. A patient return electrode is placed remotely from the active electrode to carry the current back to the generator and safely disperse current applied by the active electrode. The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on with respect to total procedure time).

Electrosurgical generators are typically comprised of power supply circuits, front panel interface circuits, and RF output stage circuits. Many electrical designs for electrosurgical generators are known in the field. In certain electrosurgical generator designs, the RF output stage can be adjusted to control the output power. The methods of controlling the RF output stage may comprise changing the duty cycle, or changing the amplitude of the driving signal to the RF output stage. The RF output may be characterized by RMS or peak-to-peak voltage, power, and/or current.

One of the effects that may be associated with electrosurgical desiccation is undesired tissue damage due to thermal effects, or thermal spread. Thermal spread may occur when healthy tissue adjacent to the operative site is undesirably affected because much too heat is allowed to build up at the operative site. Such heat may conduct to adjacent tissue and cause a region of necrosis in adjacent tissue. Thermal spread becomes a particular concern when electrosurgical tools are used in close proximity to delicate anatomical structures. Therefore, an electrosurgical generator that can better control the application of energy may reduce the occurrence or severity of thermal spread, which, in turn, may provide improved surgical outcomes and reduced operative times.

Another effect that may be associated with electrosurgical desiccation is a buildup of deposits, known as eschar, on the surgical tool. Eschar is created from tissue that is desiccated and then charred by heat. The surgical tools may lose effectiveness when the electrodes thereof become coated with eschar during use. The buildup of eschar may be reduced by controlling the heat developed at the operative site.

Arcing is yet another effect that may be associated with electrosurgical desiccation. Arcing is known in the art to be effective in cutting or dissection procedures, and may be desirable in monopolar cut modes and/or monopolar coagulation modes. However, arcing is usually undesirable in bipolar coagulation modes and/or bipolar vessel sealing modes.

Practitioners have known that a measurement of electrical impedance of tissue is a good indication of the state of desiccation of tissue, and/or the presence or absence of arcing between an electrode to tissue. Several commercially available electrosurgical generators can automatically adjust output power based on a measurement of impedance. Several methods for controlling output power in response to tissue impedance have been developed. Such control methods may exhibit uneven power delivery, such as power discontinuities and waveform distortion (e.g., glitching) when output power adjustments are performed.

SUMMARY

The present disclosure relates to a system and method for performing electrosurgical procedures. The system includes an electrosurgical generator and an instrument (e.g., electrosurgical forceps). The generator is configured to provide electrosurgical energy to the instrument, and to sense tissue impedance during an electrosurgical procedure. In response to tissue impedance and operating parameters, the generator may operate in one or more of a constant current mode, a constant power mode, and/or a constant voltage mode.

A method of operating an electrosurgical generator is also disclosed. During use the generator may be caused to transition between operating modes, or control regions, as changes in tissue impedance are sensed. As an example only, during an initial treatment phase, the generator may be operated in a constant current mode during which tissue impedance rises. At a first predetermined value of tissue impedance, the generator may transition to a constant power mode during which tissue impedance may continue to rise. At a second predetermined value of tissue impedance, the generator may transition to a constant voltage mode. The disclosed operating method includes performing the transition between operating modes in accordance with a transition function, which may be a cosine function. Additionally or alternatively, the disclosed operating method may include applying hysteresis around the transition threshold. For example, for a given transition point (e.g., at a preset impedance), a low-to-high power transition may be effectuated at an actual transition point that is higher than the given transition point. Conversely, a high-to-low power transition may be effectuated at an actual transition point that is lower than the given transition point. The use of hysteresis in this manner may help reduce or avoid instability at the transition point. Additionally or alternatively, the disclosed method may include the steps of detecting a zero crossing in an output waveform, and performing a power transition substantially concurrently therewith. The power transition may occur during at least a portion of a time window defined around a zero crossing.

In accordance with another aspect of the present disclosure, an electrosurgical system is disclosed. The system includes an electrosurgical generator adapted to supply electrosurgical energy to tissue at a power level responsive to a generator power level signal. The system also includes sensor circuitry that is adapted to continuously monitor tissue impedance and output an impedance signal in response thereto. The sensor circuitry may additionally or alternatively be adapted to sense a zero crossing of an electrosurgical generator output waveform and output a zero crossing signal in response thereto. The system includes a microprocessor operably coupled to the electrosurgical generator and the sensor circuitry that is adapted to receive at least one of an impedance signal and/or a zero crossing signal. The microprocessor is configured to output a generator power level signal, wherein the generator output signal causes the electrosurgical generator to transition from a first power level to a second power level in accordance with a transfer function. The system also includes an electrosurgical instrument including one or more active electrodes that are adapted to apply electrosurgical energy to tissue.

According to another aspect of the present disclosure, a method for performing electrosurgical procedures is disclosed. The method includes the steps of causing electrosurgical energy to be applied to tissue at a first power level. The method includes the step of sensing tissue impedance. The disclosed method additionally includes the step of determining whether tissue impedance has reached a threshold value, and in response to a determination that tissue impedance has reached a threshold value, causing the electrosurgical energy applied to tissue to transition to a second power level in accordance with a transfer function.

According to a further aspect of the present disclosure, an electrosurgical generator adapted to supply electrosurgical energy to tissue is disclosed. The disclosed electrosurgical generator includes an RF output stage adapted to supply electrosurgical energy to tissue at a power level responsive to a generator power level signal. The generator includes sensor circuitry adapted to monitor tissue impedance and output an impedance signal in response thereto. The disclosed generator also includes a microprocessor operably coupled to the electrosurgical generator and to the sensor circuitry, and adapted to receive the impedance signal. The microprocessor is further configured to output a generator power level signal, wherein the generator output signal causes the electrosurgical generator to transition from a first power level to a second power level in accordance with a transfer function. The sensor circuitry may additionally include a zero crossing detection sensor adapted to sense a zero crossing of the electrosurgical signal.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting) but merely as a basis for the claims and as a representative basis for teaching one skilled in the art to variously employ the present disclosure in virtually any appropriately detailed structure. Those skilled in the art will understand that the invention according to the present disclosure may be adapted for use with either monopolar or bipolar electrosurgical systems. In the drawings and in the descriptions that follow, the term "proximal," as is traditional, shall refer to the end of the instrument that is closer to the user, while the term "distal" shall refer to the end that is farther from the user.

Figure 1:
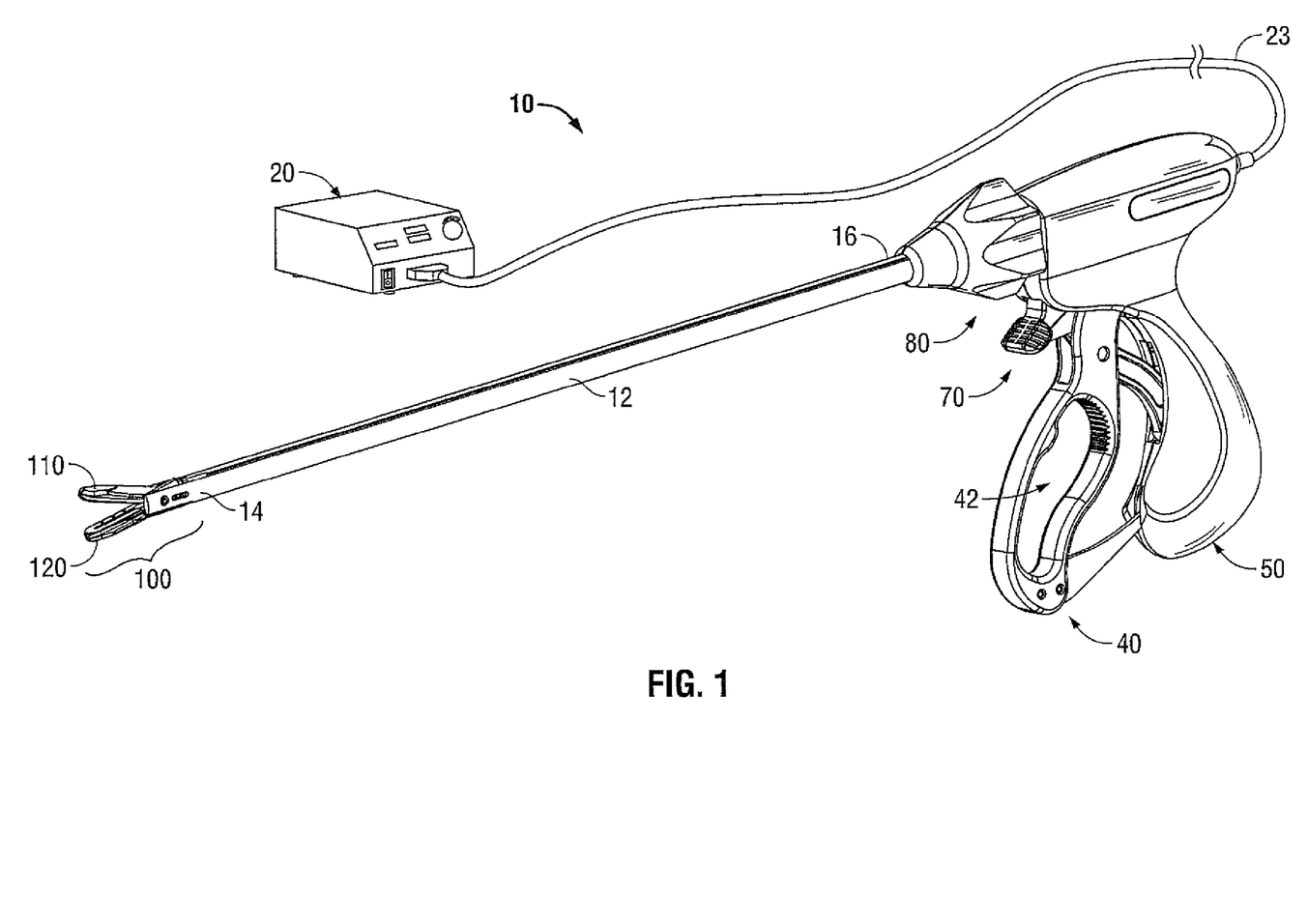
FIG. 1 shown a perspective view of an electrosurgical system in accordance with the present disclosure.

FIG. 1 shows a bipolar electrosurgical system according to the present disclosure which includes an electrosurgical forceps 10. Those skilled in the art will understand that the invention according to the present disclosure may be adapted for use with either an endoscopic instrument as shown in FIG. 1 or an open instrument. More particularly, forceps 10 generally includes a housing 21, a handle assembly 40, a rotating assembly 80, and a trigger assembly 70 which mutually cooperate with the end effector assembly 100 to grasp and treat tissue. The forceps 10 also includes a shaft 12 which has a distal end 14 that mechanically engages the end effector assembly 100 and a proximal end 16 which mechanically engages the housing 21 proximate the rotating assembly 80. Handle assembly 40 includes a fixed handle 50 and a movable handle 42. Handle 42 moves relative to the fixed handle 50 to actuate the end effector assembly 100 and enable a user to grasp and manipulate tissue. Electrosurgical RF energy is supplied to the forceps 10 by generator 20 via a supply line connected to the active electrode and returned through a return line connected to the return electrode. The supply and return lines are enclosed within a cable 23.

The generator 20 includes input controls (e.g., buttons, activators, switches, touch screen, etc.) for controlling the generator 20. In addition, the generator 20 may include one or more display screens for providing the surgeon with a variety of output information (e.g., intensity settings, treatment complete indicators, etc.). The controls allow the surgeon to adjust the RF energy, waveform, and other parameters to achieve the desired waveform suitable for a particular task (e.g., coagulating, tissue sealing, intensity setting, etc.). It is also envisioned that the forceps 10 may include a plurality of input controls which may be redundant with certain input controls of the generator 20. Placing the input controls at the forceps 10 allows for easier and faster modification of RF energy parameters during the surgical procedure without requiting interaction with the generator 20.

The end effector assembly 100 includes opposing jaw members 110 and 120 having electrically conductive sealing plates 112 and 122, respectively, attached thereto for conducting electrosurgical energy through tissue. More particularly, the jaw members 110 and 120 move in response to movement of the handle 42 from an open position to a closed position. In open position the sealing plates 112 and 122 are disposed in spaced relation relative to one another. In a clamping or closed position the sealing plates 112 and 122 cooperate to grasp tissue and apply electrosurgical energy thereto. Further details relating to one envisioned endoscopic forceps is disclosed in commonly-owned U.S. Pat. No. 7,090,673 entitled "VESSEL SEALER AND DIVIDER".

The jaw members 110 and 120 are activated using a drive assembly (not shown) enclosed within the housing 21. The drive assembly cooperates with the movable handle 42 to impart movement of the jaw members 110 and 120 from the open position to the clamping or closed position. Examples of a handle assemblies are shown and described in the above identified application as well as commonly-owned U.S. application Ser. No. 10/369,894 entitled "VESSEL SEALER AND DIVIDER AND METHOD MANUFACTURING SAME" and commonly owned U.S. Pat. No. 7,156,846 entitled "VESSEL SEALER AND DIVIDER FOR USE WITH SMALL TROCARS AND CANNULAS".

Jaw members 110 and 120 also include insulators 116 and 126 which together with the outer, non-conductive plates of the jaw members 110 and 120 are configured to limit and/or reduce many of the known undesirable effects related to tissue sealing, e.g., flashover, thermal spread and stray current dissipation.

The handle assembly 40 of this particular disclosure may include a four-bar mechanical linkage which provides a unique mechanical advantage when sealing tissue between the jaw members 110 and 120. For example, once the desired position for the sealing site is determined and the jaw members 110 and 120 are properly positioned, handle 42 may be compressed fully to lock the electrically conductive sealing plates 112 and 122 in a closed position against the tissue. The details relating to the inter-cooperative relationships of the inner-working components of forceps 10 are disclosed in the above-cited commonly-owned U.S. patent application Ser. No. 10/369,894. Another example of an endoscopic handle assembly which discloses an off-axis, lever-like handle assembly, is disclosed in the above-cited U.S. Pat. No. 7,156, 846.

The forceps 10 also includes a trigger 70 which advances a knife (not explicitly shown) disposed within the end effector assembly 100. Once a tissue seal is formed, the user activates the trigger 70 to separate the tissue along the tissue seal. Knife includes a sharpened edge for severing the tissue held between the jaw members 110 and 120 at the tissue sealing site. A longitudinally-oriented channel (not explicitly shown) is defined in an electrically conductive sealing plate 112 extending from the proximal end to the distal end thereof. The channel facilitates longitudinal reciprocation of the knife along a preferred cutting plane to effectively and accurately separate the tissue along a formed tissue seal.

The forceps 10 also includes a rotating assembly 80 mechanically associated with the shaft 12 and the drive assembly (not shown). Movement of the rotating assembly 80 imparts similar rotational movement to the shaft 12 which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. No. 10/369,894 and U.S. Pat. No. 7,156,846.

Figure 2:
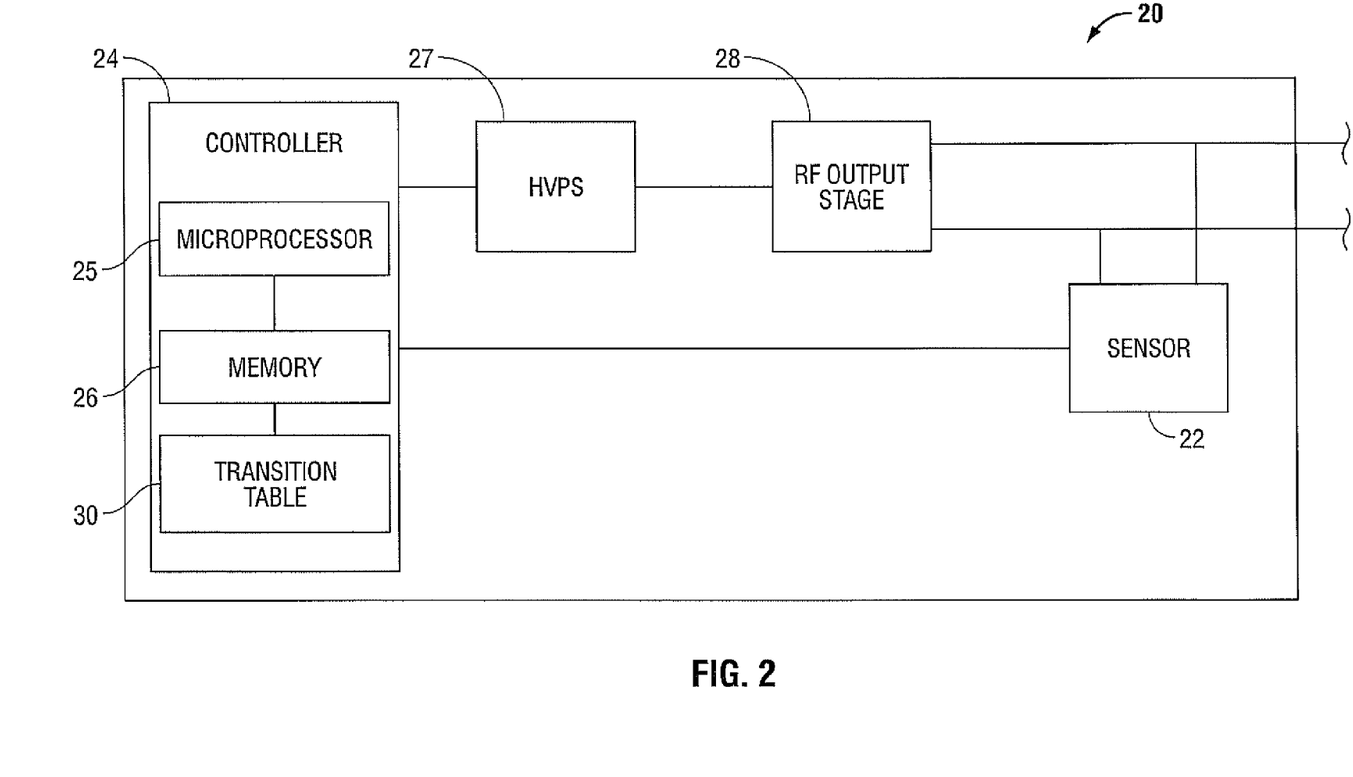
FIG. 2 is a schematic block diagram of an electrosurgical generator in accordance with the present disclosure.

As best seen with respect to FIGS. 1 and 2, the end effector assembly 100 attaches to the distal end 14 of shaft 12. The jaw members 110 and 120 are pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. No. 10/369,894 and U.S. Pat. No. 7,156,846.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 21 and handle assembly 40. In either of these two instances, the forceps 10 may be either partially disposable or reposable, such as where a new or different end effector assembly 100 or end effector assembly 100 and shaft 12 are used to selectively replace the old end effector assembly 100 as needed.

FIG. 2 shows a schematic block diagram of the generator 20 having a controller 24, a high voltage DC power supply 27 ("HVPS") and an RF output stage 28. The HVPS 27 provides high voltage DC power to an RF output stage 28 which then converts high voltage DC power into RF energy and delivers the RF energy to the active electrode 24. In particular, the RF output stage 28 generates sinusoidal waveforms of high frequency RF energy. The RF output stage 28 is configured to generate a plurality of waveforms having various duty cycles, peak voltages, crest factors, and other parameters. Certain types of waveforms are suitable for specific electrosurgical modes. For instance, the RF output stage 28 generates a 100% duty cycle sinusoidal waveform in cut mode, which is best suited for dissecting tissue and a 25% duty cycle waveform in coagulation mode, which is best used for cauterizing tissue to stop bleeding. RF output stage 28 may be configured to provide energy for monopolar and/or bipolar procedures.

The controller 24 includes a microprocessor 25 operably connected to a memory 26 which may be volatile type memory (e.g., RAM) and/or non-volatile type memory (e.g., flash media, disk media, etc.). The microprocessor 25 includes an output port which is operably connected to the HVPS 27 and/or RF output stage 28 allowing the microprocessor 25 to control the output of the generator 20 according to power delivery requirements and/or tissue impedance. The microprocessor 25 and/or memory 26 includes a set of programmed instructions configured to execute the method of performing power level transitioning as disclosed herein.

Controller 24 includes a transition lookup table 30. The transition lookup table 30 includes a succession of scaling factors (e.g., multipliers) representing the desired power level transition function. The transition function may be the cosine function. In an embodiment, the transition lookup table 30 may include about one hundred eighty entries representing the value of the cosine function from 180 to 360 degrees (e.g., π to 2π), however the transition lookup table may include any number of entries representing a transition function as expressed by the set of table entries.

Controller 24 is operably coupled to sensor circuitry 22, which may include at least one sensor that is adapted to detect and/or measure tissue impedance, output voltage, output current, output power, and/or waveform zero crossings, and communicate at least one sensor signal representing same to controller 24. The controller 24 is configured to receive the at least one sensor signal and in response thereto, causes a control signal to be communicated to HVPS 27 and/or RF output stage 28. HVPS 27 and/or RF output stage 28 is configured to receive the control signal and in response thereto regulate the output of HVPS 27 and/or RF output stage 28, respectively. The controller 24 may also receive input signals from the input controls of the generator 20 or the forceps 10. The controller 24 may utilize the input signals to adjust power outputted by the generator 20 and/or performs other control functions thereon.

Figure 3:
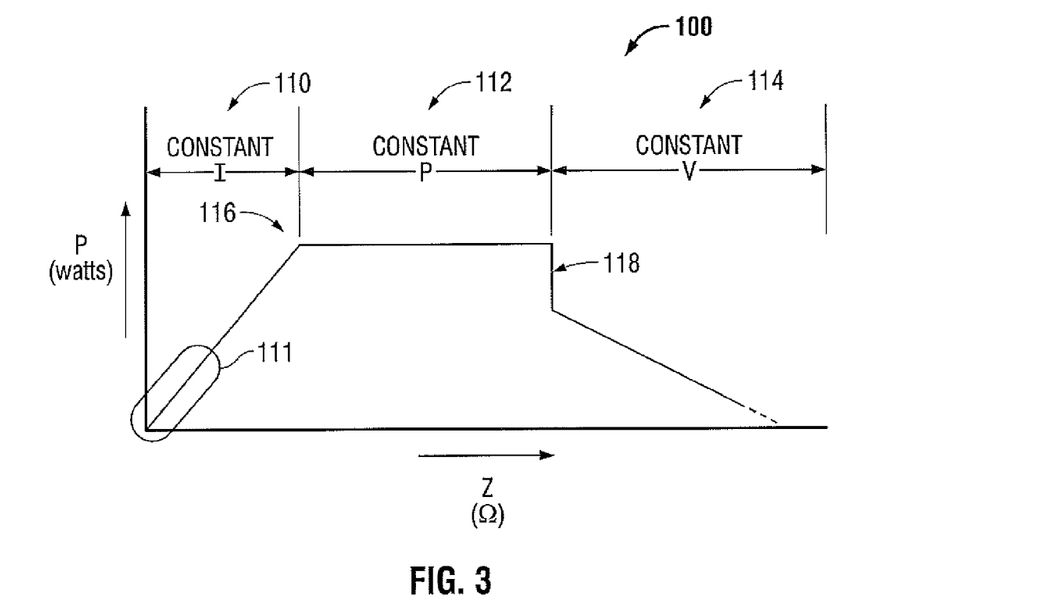
FIG. 3 is a graph depicting a relationship between power delivery and tissue impedance of an electrosurgical system in accordance with the present disclosure.

With reference now to FIG. 3, a power delivery curve 100 is shown that illustrates a desired relationship (e.g., target power curve) between an output power P of generator 20 that is delivered to tissue, and a measured tissue impedance Z, during an electrosurgical procedure, e.g., a vessel sealing procedure. The target power curve includes an initial constant current portion 110, an intermediate constant power portion 112, and a terminal constant voltage portion 114. As can be seen, during a first portion 111 of the constant current portion of the curve, the relatively low tissue impedance dictates that, initially, a lower power level be applied in order to avoid overcooking the target tissue, by causing, e.g., the formation of excessive eschar or bubble steam. Sensor 22 senses tissue impedance increases due to the heating effect of the electrosurgical energy, the controller 24 increases the power level of HVPS 27 and/or RF output stage 28 in order to maintain constant current through tissue.

During constant current portion 110 of the curve 100, energy is delivered to tissue, causing impedance to rise until an impedance value 116 corresponding to a first predetermined impedance is sensed by sensor circuitry 22. Controller 24 receives the sensor signal from sensor circuitry 22 and in response thereto, adjusts the power level of HVPS 27 and/or RF output stage 28 from a higher power ($P_h$) to a lower power ($P_l$) in accordance with the intermediate constant power portion 112 of the power delivery curve 100. The constant power portion 112 of the power delivery curve 100 is sustained, e.g., energy continues to be delivered to tissue while sensor circuitry 22 continues to monitor tissue impedance. As tissue impedance rises to an impedance value 118 corresponding to a second predetermined impedance, controller 24 receives the sensor signal from sensor circuitry 22 and in response thereto, adjusts the power level of HVPS 27 and/or RF output stage 28 in accordance with the terminal power portion (e.g., constant voltage position) 114 of the power delivery curve 100.

Figure 4:
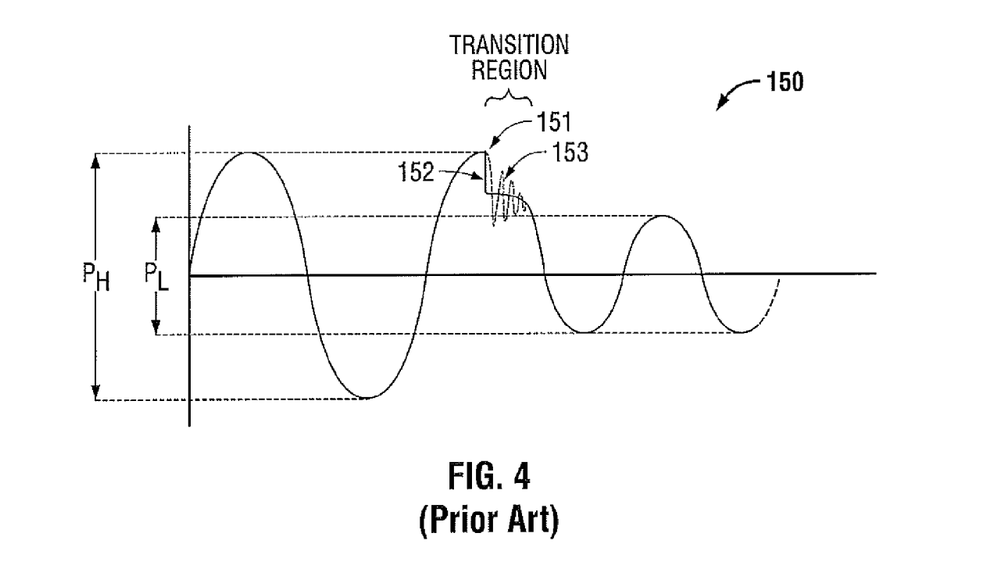
FIG. 4 illustrates an electrosurgical waveform generated by a prior art electrosurgical system.

The output of a prior art electrosurgical generator adjusting an output thereof from a first power level to a second power level, e.g., $P_h$ to $P_l$, is illustrated in FIG. 4, which depicts an output waveform 150 during a high-to-low transition. As can be seen, at a transition point 151 a prior art generator causes an output thereof to abruptly change from $P_h$ to $P_l$, e.g., the output is reduced in a substantially instantaneous step causing a discontinuity 152 in the output waveform 150. As a result, undesired high-order harmonics 153 may be generated by the rapidly falling edge of the discontinuity 152 due to resonances, ringing and/or instabilities induced in the circuit path by the abrupt prior art power transition.

Figure 5:
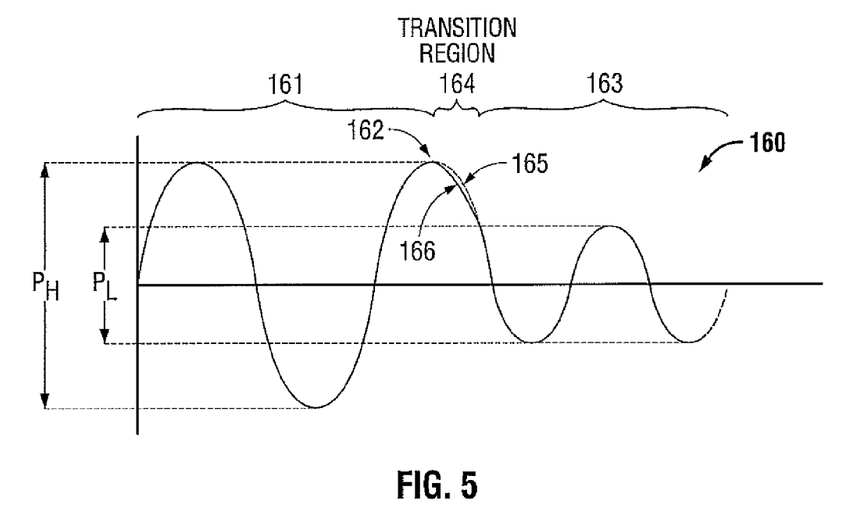
FIG. 5 illustrates an electrosurgical waveform generated by an electrosurgical system in accordance with the present disclosure.

Turning now to FIG. 5, an output waveform 160 of an electrosurgical generator in accordance with the present disclosure is presented wherein the power, e.g., amplitude, of output waveform 160 is reduced from higher power ($P_h$) region 161 to a lower power ($P_l$) region 163. Prior to a transition point 162, a software algorithm executed within controller 24 identifies a first power level (here, $P_h$), and a second power level ($P_l$) in accordance with a desired power delivery curve 100. The total desired amount of power change (ΔP) is subdivided into a predetermined number N of discrete steps, e.g., the total desired power change is performed using N smaller steps. The number of steps N may correspond to a number of entries in transition lookup table 30. Beginning at a transition point 162, controller 24 causes the generator output power to be slewed from a first power lever ($P_h$) 165 to a second power level ($P_l$) 166 smoothly over a transition region 164 in a series of successive steps in accordance with the transition function, e.g., in accordance with the factors included in the transition lookup table 30.

In greater detail, the desired total change in power may be expressed as $\Delta P = P_h - P_l$. Thus for a series of N steps, where N=180 to 360, each increment of power change may be expressed as $P_N = \Delta P f(N) + P_1$ where $f(N)$ represents the transition function. In an embodiment wherein the transfer function is a cosine function, the power change increment may be expressed as $P_N = \Delta P \cos(N) + P_1$.

Figure 6:
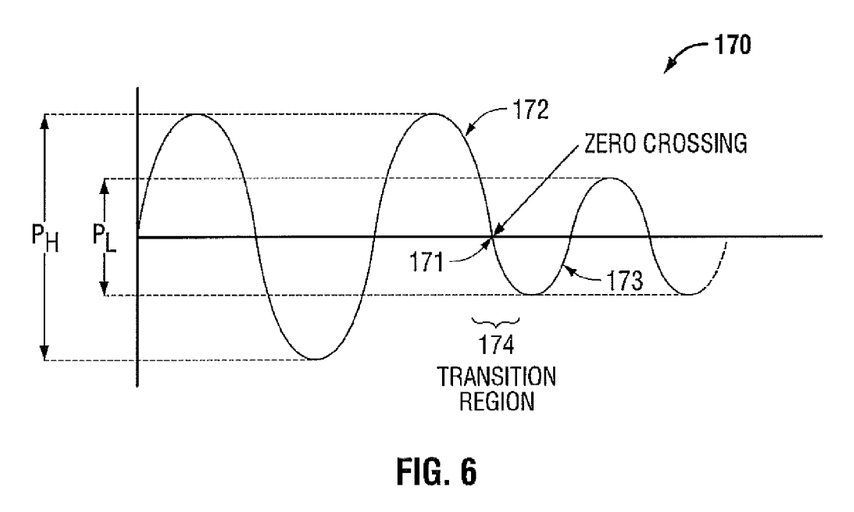
FIG. 6 illustrates another electrosurgical waveform generated by an electrosurgical system in accordance with the present disclosure.

With reference to FIG. 6, an output waveform 170 of an embodiment wherein a power transition is performed in accordance with a zero crossing power transition method is shown. Sensor circuitry 22 is adapted to detect at least one zero crossing 171 of output waveform. Additionally or alternatively, a zero crossing 171 may be identified by RF output stage 28 by, e.g., a synchronization signal (not explicitly shown) that may be generated by RF output stage 28 and/or a component thereof such as without limitation, an analog oscillator, crystal-based oscillator, or digital oscillator, or other waveform synthesis as will be familiar to the skilled artisan. Upon detecting a power transition event, e.g., a predetermined impedance threshold 116 and/or 118, a software algorithm executed within controller 24 receives a zero crossing signal from sensor circuitry 22. In response thereto, controller 24 causes the HVPS 27 and/or RF output stage 28 to transition to the power level in accordance with the target portion of the power delivery curve 100, e.g., constant current portion 110, constant power portion 112 and/or constant voltage portion 114. Performing a power transition at the zero crossing may reduce or eliminate undesirable glitching, harmonic distortion, and/or waveform discontinuities of the prior art.

In yet another embodiment, a power transition may be executed during at least a part of a transition region 174 that includes a zero crossing 171. Zero crossing 171 may be substantially centered within transition region 174. The desired power transition may be performed utilizing a stepped power transition method as described hereinabove. The combination of the disclosed stepped transition and the disclosed zero crossing transition may achieve greatly reduced levels of harmonic distortion and/or waveform discontinuities.

Figure 7:
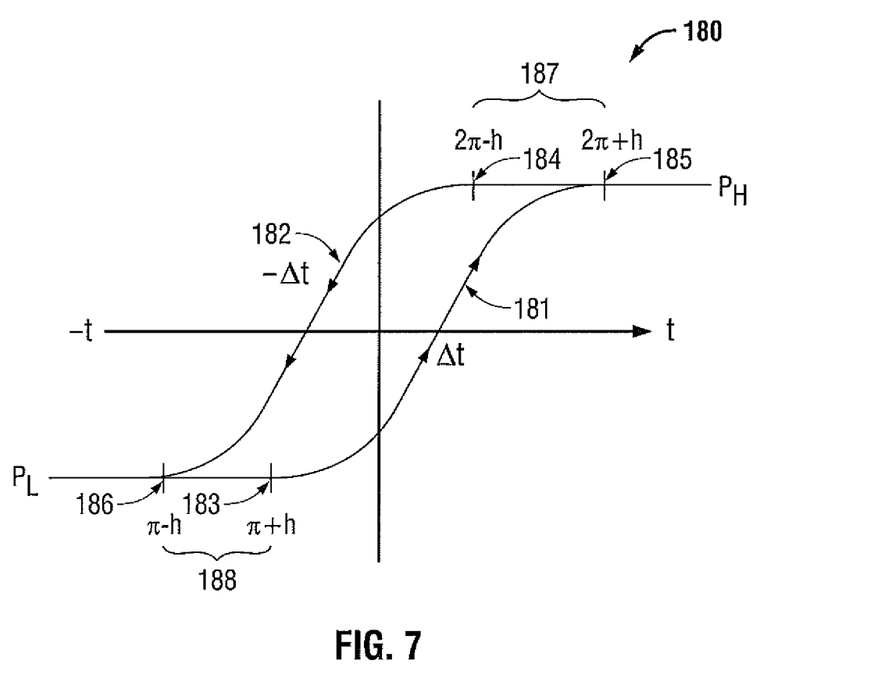
FIG. 7 is a graph depicting a power transition function in accordance with the present disclosure.

FIG. 7 illustrates generally a power level transition function 180 in accordance with the present disclosure. As can be seen, a rising (e.g., low-to-high) power level transition 181 from an initial power level $P_L$ begins at a rising start point 183 and increases substantially in accordance with a cosine function to reach a rising end point 185 corresponding to a final power level $P_H$. A falling (e.g., high-to-low) power level transition 182 begins at a falling start point 184 corresponding to a high power level $P_H$ and increases substantially in accordance with a cosine function to reach a falling end point 186 corresponding to a lower power level $P_L$. Hysteresis 187 is provided between falling start point 184 and rising end point 185, and hysteresis 188 is provided between rising start point 183 and falling start point 186. The hysteresis offset between opposing start and end points may aid in reducing instability at a transition point by e.g., reducing or eliminating chattering (uncontrolled alternation) between power levels. Hysteresis may be achieved by observing a time delay between a sensing of a tissue impedance trigger point and the initiation of a power transition associated therewith. Additionally or alternatively, hysteresis may be achieved by increasing the impedance transition point for rising power transitions and/or decreasing the impedance transition point for falling power transitions.

Figure 8:
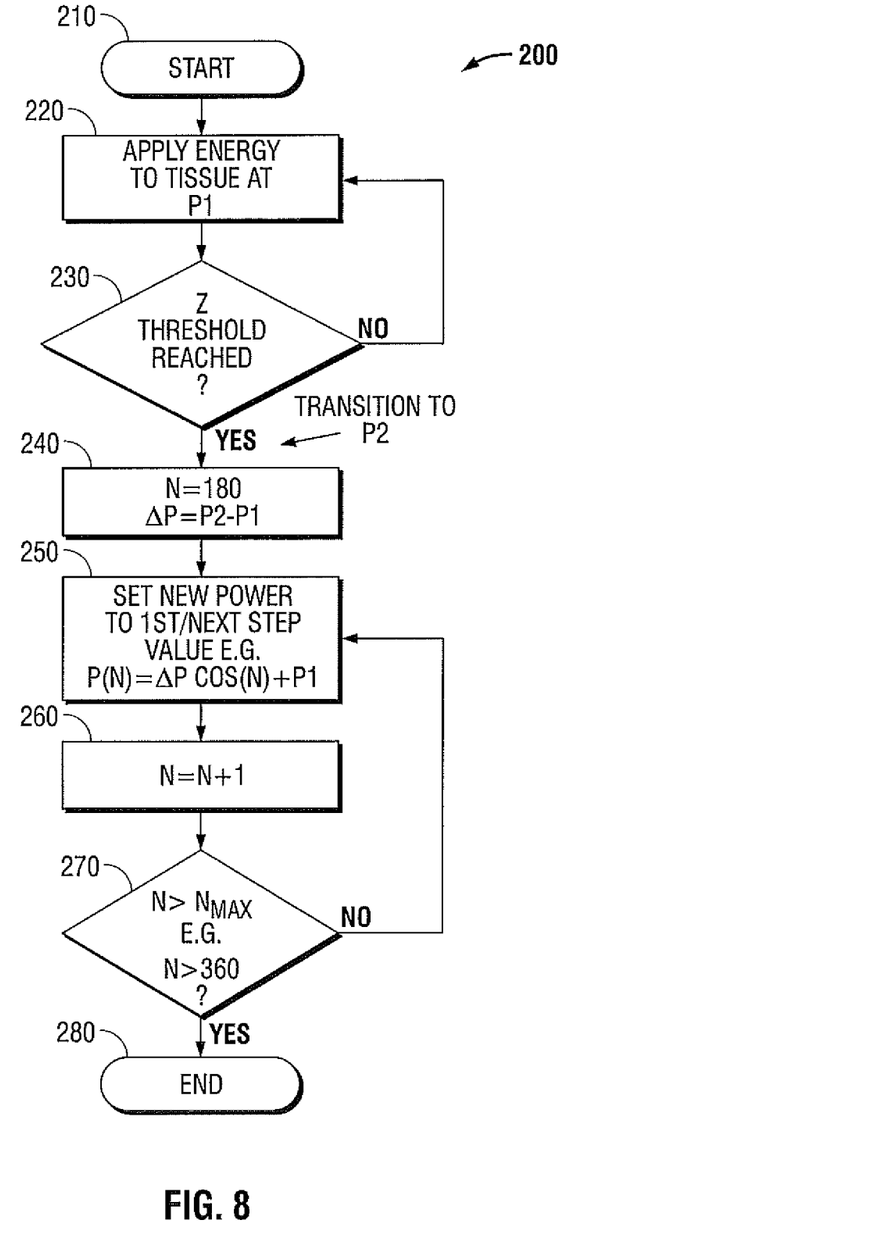
FIG. 8 is a flow diagram illustrating a method for power level transitioning in accordance with the present disclosure.

FIG. 8 illustrates a method 200 in accordance with the present disclosure for performing a power level transition in an electrosurgical instrument. The method begins with step 210 in which prefatory functions (e.g., memory allocation, loop initialization, variable initialization, and the like) may be performed. In the step 220, energy is applied to tissue at a first power level $P_1$. In the step 230, tissue impedance Z is sensed to determine if a power transition threshold is reached. If a power transition threshold is not reached in the step 230, energy continues to be applied to tissue as the step 220 and step 230 are performed iteratively. If, in the step 230 a power transition threshold is reached, the step 240 is performed wherein the transition is initialized. A loop counter N is set to an initial value, e.g., 1, and $\Delta P$ is calculated, e.g., $\Delta P = P_2 - P_1$. In the step 250, the power level is changed by an increment determined in accordance with the transition function and the number of increments into which the transition function is divided. In the present embodiment the transition function is a cosine function and the number of increments is 180 (representing e.g., 180 degrees and/or $\pi$ radians with respect to the cosine function). In the present embodiment the power level $P_N$ at increment N may be expressed as $P_N = \Delta P \cos(N) + P_1$. In the present embodiment, in the step 250 the power level is changed to $P_N$. In the step 260, loop counter N is incremented and in the step 270, the loop counter is tested to determine whether the power transition is completed, e.g., whether the loop end value has been reached. If, in the step 270 it is determined the loop end condition has not been reached, the method iterates to the step 250 wherein the power level is changed in accordance with the next increment. If, in the step 270 it is determined the loop end condition has been reached, the power transition is complete and concludes with the step 280.

Figure 9:
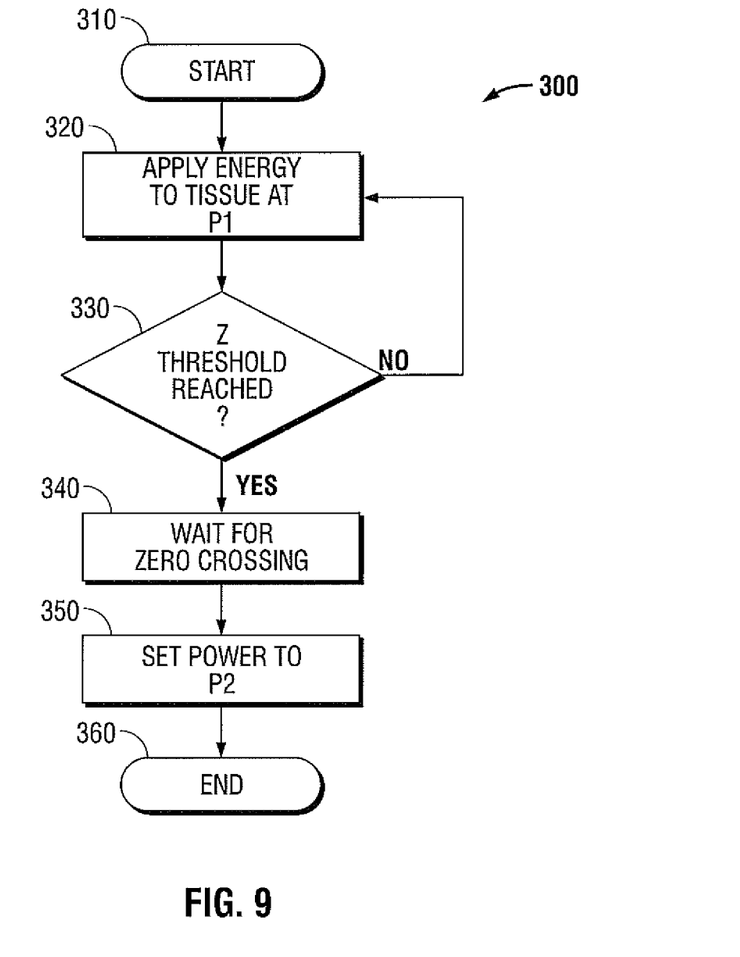
FIG. 9 is a flow diagram illustrating yet another method for power level transitioning in accordance with the present disclosure.

FIG. 9 illustrates a method 300 in accordance with the present disclosure for performing a power level transition in an electrosurgical instrument. The method begins with step 310 in which prefatory functions (e.g., memory allocation, loop initialization, variable initialization, and the like) may be performed. In the step 320, energy is applied to tissue at a first power level $P_1$. In the step 330, tissue impedance Z is sensed to determine if a power transition threshold is reached. If a power transition threshold is not reached in the step 330, energy continues to be applied to tissue as the step 320 and step 330 are performed iteratively. If, in the step 330 a power transition threshold is reached, processing proceeds to the step 340 in which the process waits for a zero crossing of an output waveform to occur. Upon occurrence of a zero crossing, in the step 350 the power level is changed from a first power level $P_1$ to a second power level $P_2$. The power transition is thus complete and concludes with the step 360.

The present disclosure contemplates that the disclosed methods may be combined wherein, upon detection of a power transition impedance threshold, the process waits for an output waveform zero crossing to occur, and a power level transition is performed in accordance with a transition function (e.g., cosine transition function as described herein). Additionally or alternatively, a power level transition may be performed in accordance with a power level transition function (e.g., cosine transition function) within a transition region 174 that encompasses a zero crossing 171.

The described embodiments of the present disclosure are intended to be illustrative rather than restrictive, and are intended be as broad in scope as the art will allow, yet are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An electrosurgical system comprising:
   an electrosurgical generator adapted to supply electrosurgical energy to tissue at a power level responsive to a generator power level signal;
   sensor circuitry adapted to monitor tissue impedance and output an impedance signal in response thereto, the sensor circuitry further adapted to monitor a zero crossing of the electrosurgical energy and output a zero crossing signal in response thereto;
   a microprocessor operably coupled to the electrosurgical generator and the sensor circuitry and adapted to receive the impedance signal and the zero crossing signal and to compare the impedance signal to an impedance transition point, and configured to output a generator power level signal, wherein the generator output signal causes the electrosurgical generator to transition from a first power level to a second power level in accordance with a transfer function defined substantially in accordance with a cosine function during a zero crossing of the electrosurgical energy;
   wherein the microprocessor is further adapted to increase the impedance transition point when the second power level is greater than the first power level and/or decrease the impedance transition point when the second power level is less than the first power level; and
   an electrosurgical instrument including at least one active electrode adapted to apply electrosurgical energy to tissue for treatment.

2. An electrosurgical system in accordance with claim 1, wherein the power level signal is output in response to a sensor signal corresponding to an impedance threshold.

3. An electrosurgical system in accordance with claim 2, wherein the impedance threshold is increased when the first power level is less than the second power level.

4. An electrosurgical system in accordance with claim 2, wherein the impedance threshold is decreased when the first power level is greater than the second power level.

5. An electrosurgical system in accordance with claim 1, wherein the electrosurgical instrument is an electrosurgical forceps for sealing tissue, the forceps comprising:
   at least one shaft member having an end effector assembly disposed at a distal end thereof, the end effector assembly including jaw members movable from a first position in spaced relation relative to one another to at least one subsequent position wherein the jaw members cooperate to grasp tissue therebetween; and a sealing plate attached to each of the jaw members in apposing relation thereto, said sealing plates adapted to connect to the electrosurgical generator such that said sealing plates communicate electrosurgical energy through tissue held therebetween.

6. A method for performing an electrosurgical procedure comprising the steps of:
   causing electrosurgical energy to be applied to tissue at a first power level;
   sensing tissue impedance;
   sensing a zero crossing of the electrosurgical energy;
   determining whether tissue impedance has reached a threshold value;
   responding to a determination that tissue impedance has reached a threshold value by causing the electrosurgical energy applied to tissue to transition to a second power level during the zero crossing in accordance with a transfer function defined substantially in accordance with a cosine function;
   increasing the threshold value when the second power level is greater than the first power level; and
   decreasing the threshold value when the second power level is less than the first power level.

7. The method in accordance with claim 6, further comprising waiting for a zero crossing of the electrosurgical energy to occur.

8. The method in accordance with claim 6, wherein the threshold value is increased when the first power level is less than the second power level.

9. The method in accordance with claim 6, wherein the threshold value is decreased when the first power level is greater than the second power level.

10. An electrosurgical generator adapted to supply electrosurgical energy to tissue, comprising:
    an RF output stage adapted to supply electrosurgical energy to tissue at a power level responsive to a generator power level signal;
    sensor circuitry adapted to monitor tissue impedance and output an impedance signal in response thereto, the sensor circuitry further adapted to monitor a zero crossing of the electrosurgical energy and output a zero crossing signal in response thereto; and
    a microprocessor operably coupled to the electrosurgical generator and the sensor circuitry and adapted to receive the impedance signal and the zero crossing signal and to compare the impedance signal to an impedance transition point, and configured to output a generator power level signal, wherein the generator output signal causes the electrosurgical generator to transition from a first power level to a second power level in accordance with a transfer function defined substantially in accordance with a cosine function during a zero crossing of the electrosurgical energy
    wherein the microprocessor is further adapted to increase the impedance transition point when the second power level is greater than the first power level and/or decrease the impedance transition point when the second power level is less than the first power level.

11. An electrosurgical generator in accordance with claim 10, wherein the power level signal is output in response to a sensor signal corresponding to an impedance threshold.

12. An electrosurgical generator in accordance with claim 11, wherein the impedance threshold is increased when the first power level is less than the second power level.

13. An electrosurgical generator in accordance with claim 11, wherein the impedance threshold is decreased when the first power level is greater than the second power level.

14. An electrosurgical generator in accordance with claim 10, wherein the electrosurgical generator is connected an electrosurgical instrument including at least one active electrode adapted to apply electrosurgical energy to tissue.

15. An electrosurgical generator in accordance with claim 14, wherein the electrosurgical instrument is an electrosurgical forceps for sealing tissue, the forceps comprising:
    at least one shaft member having an end effector assembly disposed at a distal end thereof, the end effector assembly including jaw members movable from a first position in spaced relation relative to one another to at least one subsequent position wherein the jaw members cooperate to grasp tissue therebetween; and
    a sealing plate attached to each of the jaw members in apposing relation thereto, said sealing plates adapted to connect to the electrosurgical generator such that said sealing plates communicate electrosurgical energy through tissue held therebetween.

* * * * *